United States Patent
Paillaman et al.

(10) Patent No.: US 6,865,243 B2
(45) Date of Patent: Mar. 8, 2005

(54) METHOD OF DETECTING CRACKS IN JET PUMP BEAMS OF A NUCLEAR REACTOR

(75) Inventors: Rodolfo Paillaman, Huntersville, NC (US); Trevor Davis, Charlotte, NC (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 10/065,516

(22) Filed: Oct. 25, 2002

(65) Prior Publication Data

US 2004/0081267 A1 Apr. 29, 2004

(51) Int. Cl.[7] .............................................. G21C 17/00
(52) U.S. Cl. ......................... 376/245; 376/372; 73/570
(58) Field of Search ................................ 376/245, 372, 376/249; 73/570

(56) References Cited

U.S. PATENT DOCUMENTS

| | | | |
|---|---|---|---|
| 4,394,345 A | 7/1983 | De Briere et al. | |
| 4,531,663 A | 7/1985 | Kajiyama et al. | |
| 5,194,215 A | 3/1993 | Nachbar et al. | |
| 5,568,527 A | 10/1996 | Richardson et al. | |
| 5,710,378 A | 1/1998 | Dykes et al. | |
| 5,864,595 A | 1/1999 | Burrows et al. | |
| 6,082,198 A | * 7/2000 | Sabourin et al. | ............... 73/633 |
| 6,137,853 A | 10/2000 | Duckering et al. | |
| 6,186,948 B1 | * 2/2001 | Kamiyama et al. | ......... 600/443 |
| 6,332,011 B1 | * 12/2001 | Johnson | ...................... 376/249 |

* cited by examiner

Primary Examiner—Michael J. Carone
Assistant Examiner—Rick Palabrica
(74) Attorney, Agent, or Firm—Armstrong Teasdale LLP

(57) ABSTRACT

A method of inspecting a jet pump beam in a nuclear reactor is provided. The reactor includes at least one jet pump assembly with each jet pump assembly including at least one jet pump beam. Each jet pump beam includes a beam bolt opening, a first arm, a second arm, a top surface, and a bottom surface. In an exemplary embodiment, the method includes positioning at least one ultrasonic phased array probe adjacent the bottom surface of the jet pump beam, and scanning the jet pump beam with the at least one ultrasonic phased array probe.

19 Claims, 5 Drawing Sheets

METHOD OF DETECTING CRACKS IN JET PUMP BEAMS OF A NUCLEAR REACTOR

BACKGROUND OF INVENTION

This invention relates generally to inspection of nuclear reactors, and more particularly to ultrasonic examination of jet pump beams within a nuclear reactor pressure vessel.

A reactor pressure vessel (RPV) of a boiling water reactor (BWR) typically has a generally cylindrical shape and is closed at both ends, e.g., by a bottom head and a removable top head. A top guide typically is spaced above a core plate within the RPV. A core shroud, or shroud, typically surrounds the core and is supported by a shroud support structure. Particularly, the shroud has a generally cylindrical shape and surrounds both the core plate and the top guide. There is a space or annulus located between the cylindrical reactor pressure vessel and the cylindrically shaped shroud.

In a BWR, hollow tubular jet pumps positioned within the shroud annulus provide the required reactor core water flow. The upper portion of the jet pump, known as the inlet mixer, is laterally positioned and supported against two opposing rigid contacts within restrainer brackets by a gravity actuated wedge. The inlet mixers are each held in place at the top end by a preloaded beam. To secure the assembly, the jet pump beam is assembled with a high preload, applied by installing the jet pump beam bolt with a hydraulic tensioner.

The static and dynamic loads on jet pump beams including vibrations imposed during reactor operation have been found to cause, in some instances, beam cracking that begins in the upper central portion of the beams. Each jet pump beam holds in place a pipe elbow, which leads reactor water from an inlet riser pipe toward a jet pump nozzle.

Cracking in a jet pump beam threatens the release of a pipe elbow from its normal position, which could impair proper jet pump operation. Accordingly, it is desirable to determine the physical integrity of jet pump beams on a regular basis, as for example by ultrasonic examination. In some cases, this is done by dismantling the jet pump beams from the reactor and transporting them to a laboratory for testing. In other cases, an ultrasonic on-site inspection of the jet pump beams within the reactor vessel is performed.

SUMMARY OF INVENTION

In one aspect, a method of inspecting a jet pump beam in a nuclear reactor is provided. The reactor includes at least one jet pump assembly with each jet pump assembly including at least one jet pump beam. Each jet pump beam includes a beam bolt opening, a first arm, a second arm, a top surface, and a bottom surface. The method includes positioning at least one ultrasonic phased array probe adjacent the bottom surface of the jet pump beam, and scanning the jet pump beam with the at least one ultrasonic phased array probe.

In another aspect, a method of inspecting a jet pump beam in a nuclear reactor is provided. The reactor includes at least one jet pump assembly with each jet pump assembly including at least one jet pump beam. Each jet pump beam includes a beam bolt opening, a first arm, a second arm, a top surface, and a bottom surface. Each beam arm has a transition portion and a radiused portion located adjacent the transition portion. The method includes positioning at least one ultrasonic phased array probe adjacent the bottom surface of the jet pump beam, and scanning at least one of the transition portion and the radiused portion of each beam arm with the at least one ultrasonic phased array probe.

DETAILED DESCRIPTION

Figure 1:
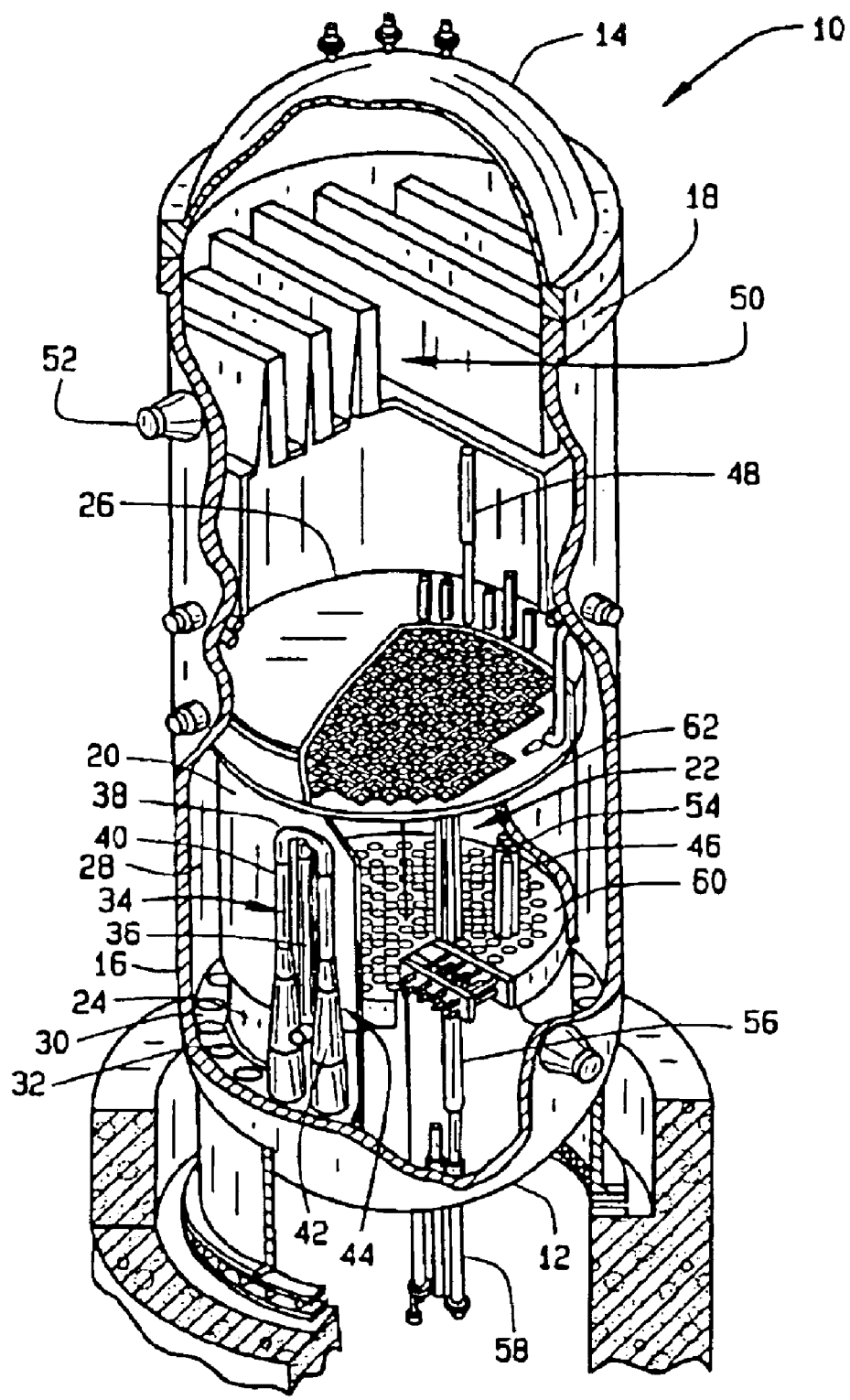
FIG. 1 is a sectional view, with parts cut away, of a boiling water nuclear reactor pressure vessel.

FIG. 1 is a sectional view, with parts cut away, of a boiling water nuclear reactor pressure vessel (RPV) 10. RPV 10 has a generally cylindrical shape and is closed at one end by a bottom head 12 and at its other end by a removable top head 14. A side wall 16 extends from bottom head 12 to top head 14. Side wall 16 includes a top flange 18. Top head 14 is attached to top flange 18. A cylindrically shaped core shroud 20 surrounds a reactor core 22. Shroud 20 is supported at one end by a shroud support 24 and includes a removable shroud head 26 at the other end. An annulus 28 is formed between shroud 20 and side wall 16. A pump deck 30, which has a ring shape, extends between shroud support 24 and RPV side wall 16. Pump deck 30 includes a plurality of circular openings 32, with each opening housing a jet pump 34. Jet pumps 34 are circumferentially distributed around core shroud 20. An inlet riser pipe 36 is coupled to two jet pumps 34 by a transition assembly 38. Each jet pump 34 includes an inlet mixer 40, and a diffuser 42. Inlet riser 36 and two connected jet pumps 34 form a jet pump assembly 44.

Heat is generated within core 22, which includes fuel bundles 46 of fissionable material. Water circulated up through core 22 is at least partially converted to steam. Steam separators 48 separates steam from water, which is recirculated. Residual water is removed from the steam by steam dryers 50. The steam exits RPV 10 through a steam outlet 52 near vessel top head 14.

The amount of heat generated in core 22 is regulated by inserting and withdrawing control rods 54 of neutron absorbing material, such as for example, hafnium. To the extent that control rod 54 is inserted into fuel bundle 46, it absorbs neutrons that would otherwise be available to promote the chain reaction which generates heat in core 22. Control rod guide tubes 56 maintain the vertical motion of control rods 54 during insertion and withdrawal. Control rod drives 58 effect the insertion and withdrawal of control rods 54. Control rod drives 58 extend through bottom head 12.

Fuel bundles 46 are aligned by a core plate 60 located at the base of core 22. A top guide 62 aligns fuel bundles 46 as they are lowered into core 22. Core plate 60 and top guide 62 are supported by core shroud 20.

Figure 2:
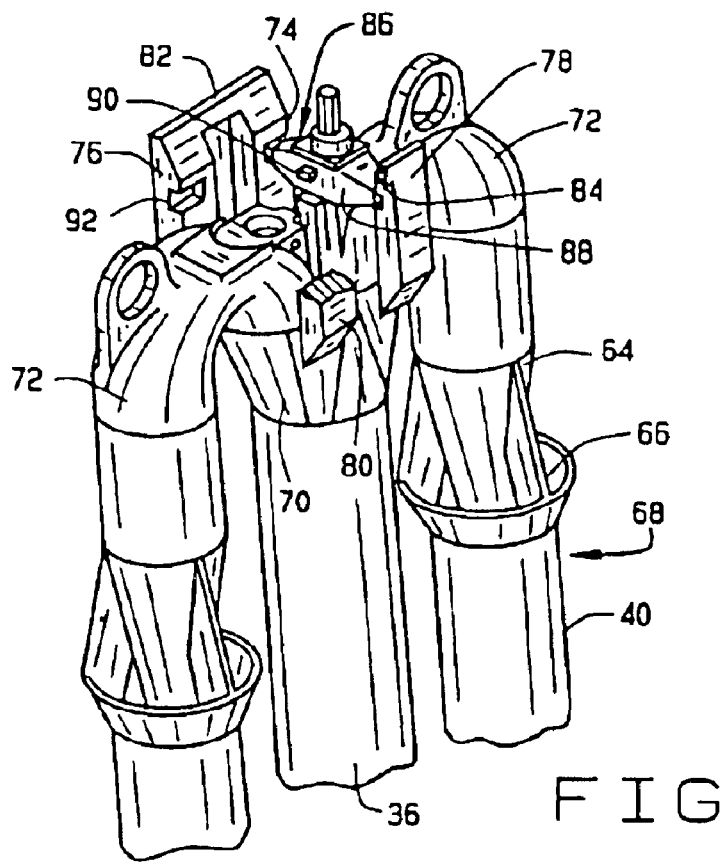
FIG. 2 is a perspective view, with parts cut away, of a jet pump assembly shown in FIG. 1.

FIG. 2 is a perspective view, with parts cut away, of jet pump assembly 44. Jet pump assembly 44 includes riser pipe 36 coupled to a pair of jet pumps 34 by transition assembly 38. Each jet pump 34 includes a jet pump nozzle 64, a suction inlet 66, an inlet mixer 40, and a diffuser 42 (shown in FIG. 1). Jet pump nozzle 64 is positioned in suction inlet 66 which is located at a first end 68 of inlet mixer 40.

Figure 3:
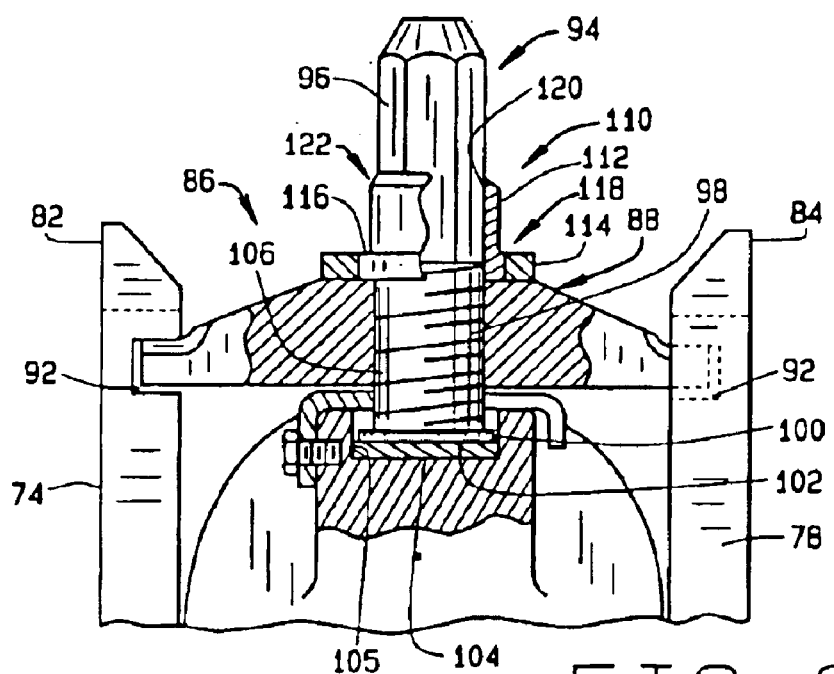
FIG. 3 is a side view of the jet pump beam shown in FIG. 2.

Transition assembly 38 includes a base piece 70 and two elbows 72. Each elbow 72 is coupled to a jet pump nozzle 64. Support arms 74, 76, 78, and 80 extend from transition assembly base piece 70. Cross beam 82 connects support arms 74 and 76, and cross beam 84 (partially cut away in FIG. 2) connects support arms 78 and 80. A jet pump beam 86 extends between support arms 74 and 78. An identical jet pump beam (not shown) extends between support arms 76 and 80. Referring also to FIG. 3, jet pump beam 86 includes a raised central portion 88 and trunions 90. The ends of jet pump beam 86 are supported in notches 92 located in support beams 74 and 78. A beam bolt 94 includes a multisided head 96, a threaded portion 98, and a butt end 100 including a lower bearing surface 102 which bears against a disc 104 seated in a counter bore 105 of elbow 72. Beam bolt 94 threadedly engages a threaded bolt opening 106 in jet pump beam 86.

A locking assembly 110 prevents beam bolt 94 from loosening. Locking assembly 110 includes a locking sleeve 112 and a lock plate 114. Locking sleeve 112 includes a base portion 116 at a first end 118 and a bore 120 extending from first end 118 to a second end 122. Bore 120 is sized and shaped to matingly receive beam bolt head 96.

Figure 4:
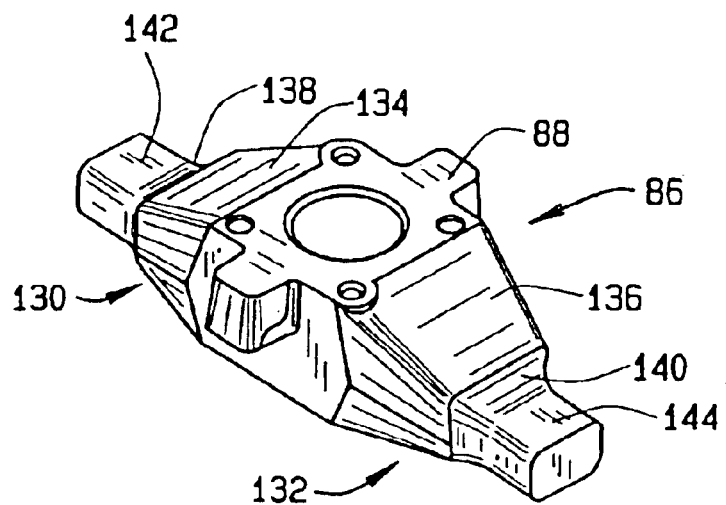
FIG. 4 is a perspective view of the jet pump beam shown in FIG. 3.

Referring to FIG. 4, jet pump beam 86 includes a first beam arm 130 and a second beam arm 132. Beam arms 130 and 132 include transition portions 134 and 136 respectively extending from central portion 88. Radiused portions 138 and 140 extend from transition portions 134 and 136 respectively and joins beam arm end portions 142 and 144 to transition portions 134 and 136 respectively. Threaded bolt opening 106 extends through central portion 88.

Figure 7:
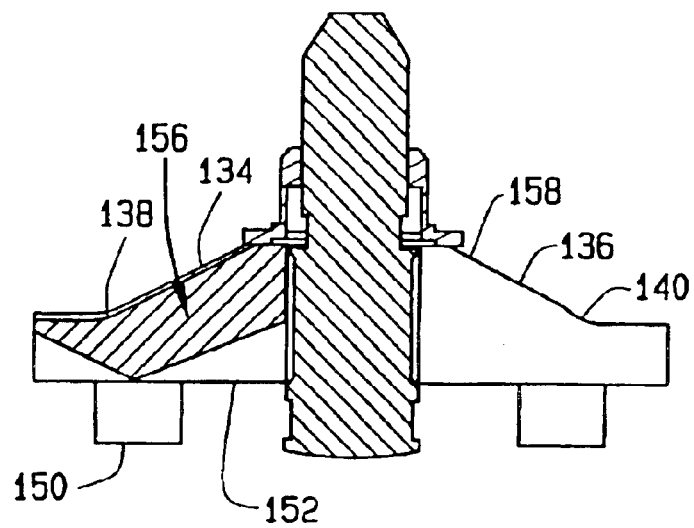
FIG. 7 is sectional view of the jet pump beam shown in FIG. 6.
Figure 5:
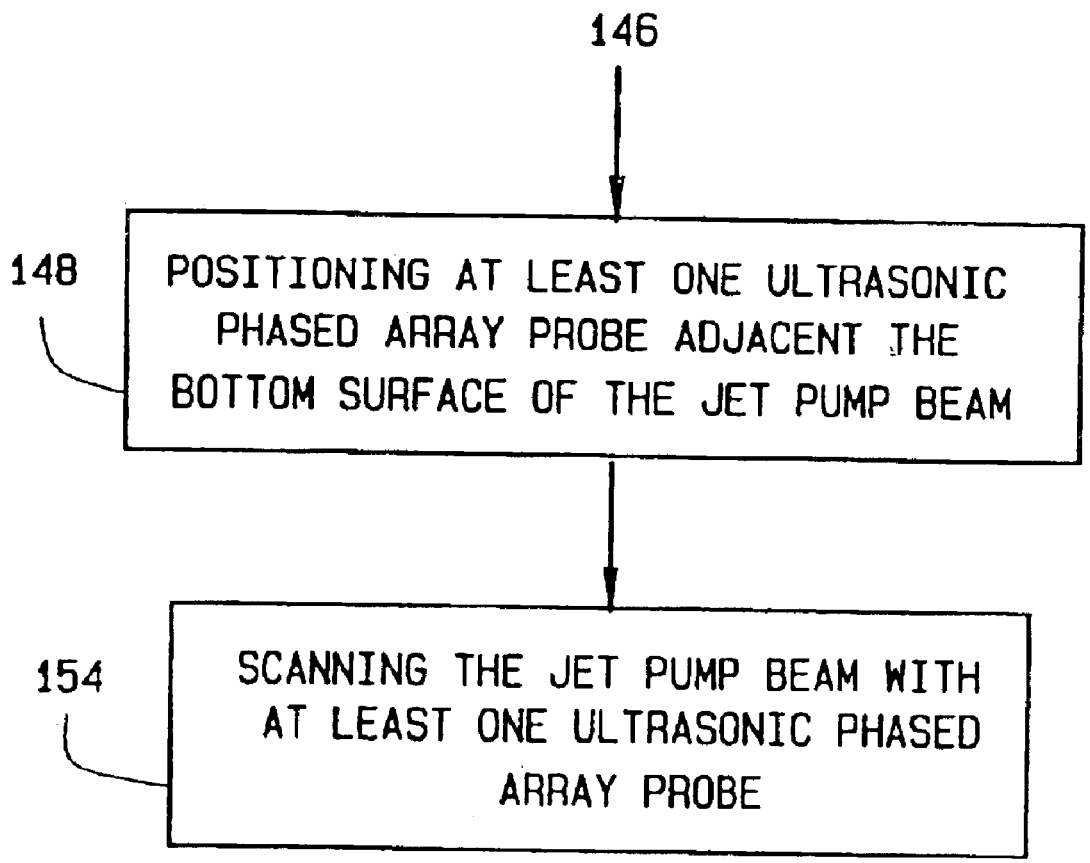
FIG. 5 is a flow chart of a method of inspecting the jet pump beam in accordance with an embodiment of the present invention.
Figure 6:
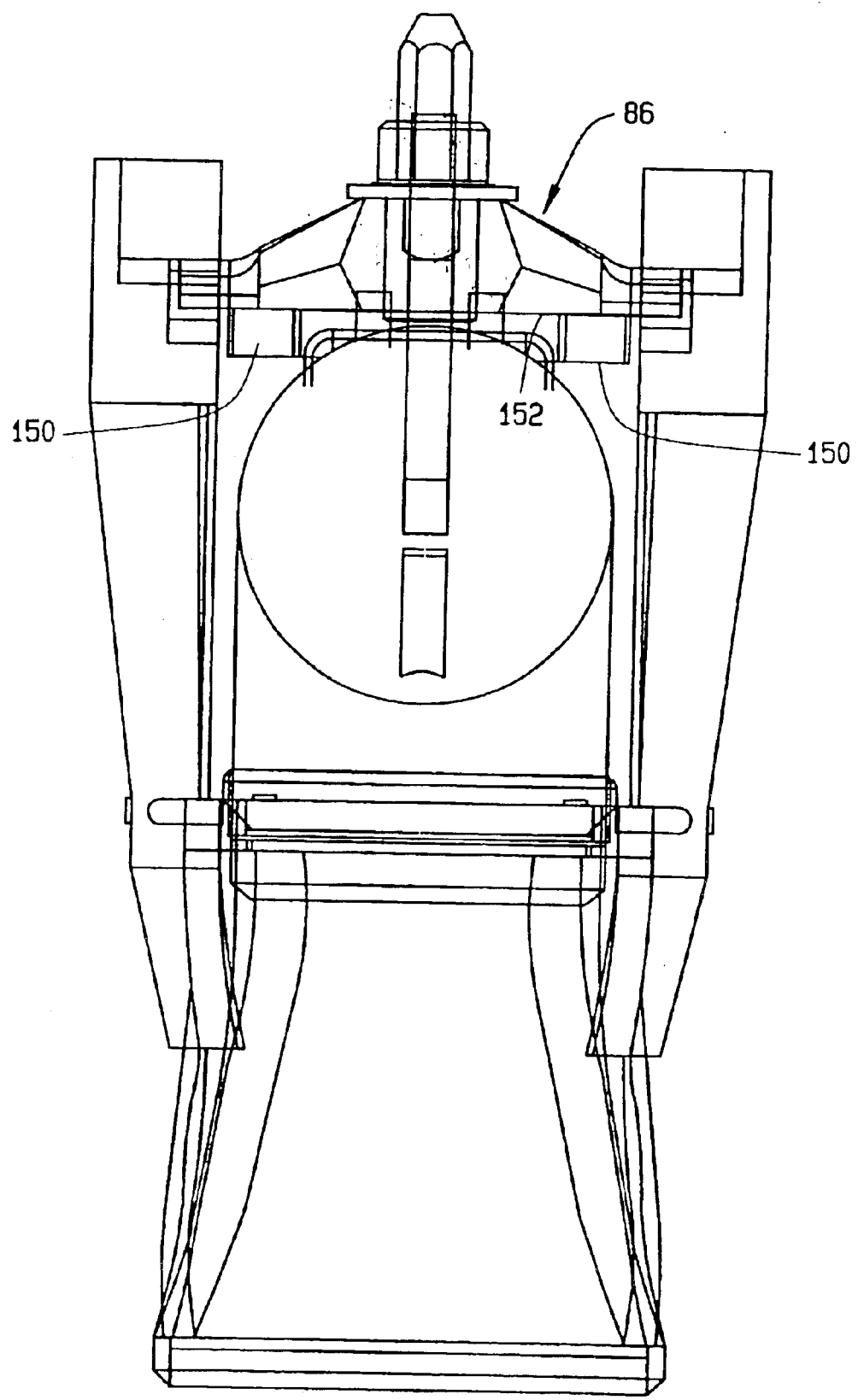
FIG. 6 is a schematic side view of the jet pump assembly shown in FIG. 1 showing the placement of ultrasonic phased array probes.

Referring to FIGS. 5, 6 and 7, in an exemplary embodiment, a method 146 of inspecting jet pump beam 86 includes positioning 148 at least one ultrasonic phased array probe 150 adjacent a lower surface 152 of beam 86 and scanning 154 beam 86 with the at least one probe 150.

Particularly, the positioning of ultrasonic phased array probes 150 on lower surface 152 of beam 86, permits an ultrasonic examination of central portion 88, threaded bolt opening 106, and also transition portions 134 and 136, and radiused portions 138 and 140 of beam arms 130 and 132. As shown in FIG. 6, the volume 156 of beam 86 that is examined includes the area of central portion 88, transition portions 138 and 140 and the area of radiused portions 134 and 136, and extending from a upper surface 158 of beam 86 towards lower surface 152.

Ultrasonic phased array probes exhibit advantages over standard ultrasonic probes. A phased array probe is formed from an array of transducer elements in a single housing. The elements in the array are smaller than a single element probe which provides for larger beam divergence angles of each element and permits dynamic focusing and beam steering. Also the small elements in an array are more energy efficient and take less energy to excite and are more efficient receivers due to the lower mass to be energized. An important aspect of array usage is the ability to dynamically synthesize an ultrasonic beam and create a "Virtual Probe" of any angle within the overall beam spread of an individual element. An angle beam is created by sequentially firing each element in an array to create a wave front following the desired angle. The angle is selected and set up electronically by the control instrumentation, and can if necessary be changed pulse by pulse. This "Virtual Probe" can also be "swept" through a test object by firing groups of elements in a large array. This effect can be used to dynamically focus an ultrasonic beam by selecting the array firing order and pulse delays. This can be changed on a pulse by pulse basis to effectively "sweep" a focal point through test material. Beam steering and dynamic focusing can be combined to give a resultant beam which is both focused and angled. Ultrasonic phased array probes are commercially available from Krautkramer Ultrasonic Systems Group of Agfa NDT, Inc., Lewistown, Pa.

In the exemplary embodiment, positioning 148 at least one ultrasonic phased array probe 150 adjacent a lower surface 152 of beam 86 includes positioning a first ultrasonic phased array probe 150 adjacent a lower surface 152 of beam 86 in alignment with first beam arm 130 and positioning a second ultrasonic phased array probe 150 adjacent a lower surface 152 of beam 86 in alignment with second beam arm 132.

In another embodiment, an ultrasonic examination of jet pump beam 86 is accomplished by positioning an ultrasonic phased array probe 150 adjacent a lower surface 152 of beam 86 in alignment with first beam arm 130. Central portion 88, including threaded bolt opening 106 of beam 86, and transition portion 134 and radiused portion 138 of first beam arm 130 are then scanned with probe 150. Next, probe 150 is repositioned adjacent lower surface 152 of beam 86 in alignment with second beam arm 132. Central portion 88, including threaded bolt opening 106 of beam 86, and transition portion 136 and radiused portion 140 of second beam arm 132 are then scanned with probe 150.

In another embodiment, an ultrasonic examination of adjacent jet pump beams 86 of jet pump assembly 44 is accomplished by positioning a first ultrasonic phased array probe 150 adjacent lower surface 152 of one beam 86 in alignment with first beam arm 130, and a second ultrasonic phased array probe 150 adjacent lower surface 152 of the adjacent beam 86 in alignment with first beam arm 130. Central portions 88, including threaded bolt openings 106 of adjacent beams 86, and transition portion 134 and radiused portion 138 of first beam arms 130 are then scanned with probes 150. Next, probes 150 are repositioned adjacent lower surface 152 of first beam 86 and adjacent beam 86 in alignment with second beam arms 132. Central portions 88, including threaded bolt openings 106 of adjacent beams 86, and transition portions 136 and radiused portions 140 of second beam arms 132 are then scanned with probes 150.

In a further embodiment, an ultrasonic examination of adjacent jet pump beams 86 of jet pump assembly 44 is accomplished by positioning a first ultrasonic phased array probe 150 adjacent lower surface 152 of one beam 86 in alignment with first beam arm 130, a second ultrasonic phased array probe 150 adjacent lower surface 152 of beam 86 in alignment with second beam arm 132, a third ultrasonic phased array probe 150 adjacent lower surface 152 of the adjacent beam 86 in alignment with first beam arm 130, and a fourth ultrasonic phased array probe 150 adjacent lower surface 152 of the adjacent beam 86 in alignment with second beam arm 132. Central portions 88, including threaded bolt openings 106 of adjacent beams 86, and transition portion 134 and radiused portion 138 of first and second beam arms 130 and 132 are then scanned with probes 150.

The above described method 146 of inspecting jet pump beam 86 using ultrasonic phased array probe 150 permits the inspection of transition portions 134 and 136 and radiused portions 138 and 140 of beam arms 130 and 132 with one placement of probe 150 under each beam arm 130 and 132.

This results in a more complete and more reliable examination of jet pump beam 86.

While the invention has been described in terms of various specific embodiments, those skilled in the art will recognize that the invention can be practiced with modification within the spirit and scope of the claims.

What is claimed is:

1. A method of inspecting a jet pump beam in a nuclear reactor, the reactor comprising at least one jet pump assembly with each jet pump assembly comprising at least one jet pump beam, each jet pump beam comprising a beam bolt opening, a first arm, a second arm, a top surface, and a bottom surface, said method comprising:

positioning at least one ultrasonic phased array probe adjacent the bottom surface of the jet pump beam, wherein the at least one ultrasonic phased array probe is positioned under the bottom surface of the jet pump beam; and scanning the jet pump beam with the at least one ultrasonic phased array probe so that a scanned volume of the jet pump beam comprises an area extending from the bolt opening to the end of the first beam arm and that extends from the top surface of the beam at least partially towards the bottom of the beam.

2. A method in accordance with claim 1 wherein positioning at least one ultrasonic phased array probe comprises positioning a first ultrasonic phased array probe adjacent the bottom surface of the jet pump beam first arm, said method further comprising:

scanning the jet pump beam first arm with the first ultrasonic phased array probe;

re-positioning the first ultrasonic phased array probe adjacent the bottom surface of the jet pump beam second arm; and scanning the jet pump beam second arm with the first ultrasonic phased array probe.

3. A method in accordance with claim 1 wherein positioning at least one ultrasonic phased array probe comprises:

positioning a first ultrasonic phased array probe adjacent the bottom surface of the jet pump beam first arm; and positioning a second ultrasonic phased array probe adjacent the bottom surface of the jet pump beam second arm.

4. A method in accordance with claim 3 wherein scanning the jet pump beam comprises:

scanning the jet pump beam first arm with the first ultrasonic phased array probe; and scanning the jet pump beam second arm with the second ultrasonic phased array probe.

5. A method in accordance with claim 1 wherein each jet pump assembly comprises a first jet pump beam and a second jet pump beam, and positioning at least one ultrasonic phased array probe adjacent the bottom surface of the jet pump beam comprises:

positioning a first ultrasonic phased array probe adjacent the bottom surface of the first jet pump beam first arm; and positioning a second ultrasonic phased array probe adjacent the bottom surface of the second jet pump beam first arm.

6. A method in accordance with claim 5 wherein scanning the jet pump beam comprises:

scanning the first jet pump beam first arm with the first ultrasonic phased array probe;

scanning the second jet pump beam first arm with the second ultrasonic phased array probe;

re-positioning the first ultrasonic phased array probe adjacent the bottom surface of the first jet pump beam second arm;

re-positioning the second ultrasonic phased array probe adjacent the bottom surface of the second jet pump beam second arm;

scanning the first and second jet pump beam second arms with the first and second ultrasonic phased array probes respectively.

7. A method in accordance with claim 1 wherein each jet pump assembly comprises a first jet pump beam and a second jet pump beam, and positioning at least one ultrasonic phased array probe adjacent the bottom surface of the jet pump beam comprises:

positioning a first ultrasonic phased array probe adjacent the bottom surface of the first jet pump beam first arm;

positioning a second ultrasonic phased array probe adjacent the bottom surface of the first jet pump beam second arm;

positioning a third ultrasonic phased array probe adjacent the bottom surface of the second jet pump beam first arm; and positioning a fourth ultrasonic phased array probe adjacent the bottom surface of the second jet pump beam second arm.

8. A method in accordance with claim 7 wherein scanning the jet pump beam comprises:

scanning the first jet pump beam first arm with the first ultrasonic phased array probe;

scanning the first jet pump beam second arm with the second ultrasonic phased array probe;

scanning the second jet pump beam first arm with the third ultrasonic phased array probe;

scanning the second jet pump beam second arm with the fourth ultrasonic phased array probe.

9. A method in accordance with claim 1 wherein scanning the jet pump beam further comprises scanning the jet pump beam with the at least one ultrasonic phased array probe so that a scanned volume of the jet pump beam further comprises an area extending from the bolt opening to the end of the second beam arm and extending from the top surface of the beam at least partially towards the bottom of the beam.

10. A method of inspecting a jet pump beam in a nuclear reactor, the reactor comprising at least one jet pump assembly with each jet pump assembly comprising at least one jet pump beam, each jet pump beam comprising a beam bolt opening, a first arm, a second arm, a top surface, and a bottom surface, each beam arm comprising a transition portion and a radiused portion located adjacent the transition portion, said method comprising:

positioning at least one ultrasonic phased array probe adjacent the bottom surface of the jet pump beam, wherein the at least one ultrasonic phased array probe is positioned under the bottom surface of the jet pump beam; and scanning at least one of the transition portion and the radiused portion of each jet pump beam arm with the at least one ultrasonic phased array probe so that a scanned volume of the jet pump beam comprises an area extending from the bolt opening to an end of the at least one of the transition portion and the radiused portion of each jet pump beam arm, and that extends from the top surface of the beam at least partially towards the bottom of the beam.

11. A method in accordance with claim 10 wherein positioning at least one ultrasonic phased array probe comprises positioning a first ultrasonic phased array probe adjacent the bottom surface of the jet pump beam first arm, and said method further comprising:

scanning at least one of the transition portion and the radiused portion of the jet pump beam first arm with the first ultrasonic phased array probe;

re-positioning the first ultrasonic phased array probe adjacent the bottom surface of the jet pump beam second arm; and scanning at least one of the transition portion and the radiused portion of the jet pump beam second arm with the first ultrasonic phased array probe.

12. A method in accordance with claim 10 wherein positioning at least one ultrasonic phased array probe comprises:

positioning a first ultrasonic phased array probe adjacent the bottom surface of the jet pump beam first arm; and positioning a second ultrasonic phased array probe adjacent the bottom surface of the jet pump beam second arm.

13. A method in accordance with claim 12 wherein scanning the jet pump beam comprises:

scanning at least one of the transition portion and the radiused portion of the jet pump beam first arm with the first ultrasonic phased array probe; and scanning at least one of the transition portion and the radiused portion of the jet pump beam second arm with the second ultrasonic phased array probe.

14. A method in accordance with claim 10 wherein each jet pump assembly comprises a first jet pump beam and a second jet pump beam, and positioning at least one ultrasonic phased array probe adjacent the bottom surface of the jet pump beam comprises:

positioning a first ultrasonic phased array probe adjacent the bottom surface of the first jet pump beam first arm; and positioning a second ultrasonic phased array probe adjacent the bottom surface of the second jet pump beam first arm.

15. A method in accordance with claim 14 wherein scanning the jet pump beam comprises:

scanning at least one of the transition portion and the radiused portion of the first jet pump beam first arm with the first ultrasonic phased array probe;

scanning at least one of the transition portion and the radiused portion of the second jet pump beam first arm with the second ultrasonic phased array probe;

re-positioning the first ultrasonic phased array probe adjacent the bottom surface of the first jet pump beam second arm;

re-positioning the second ultrasonic phased array probe adjacent the bottom surface of the second jet pump beam second arm;

scanning at least one of the transition portion and the radiused portion of the first and second jet pump beam second arms with the first and second ultrasonic phased array probes respectively.

16. A method in accordance with claim 10 wherein each jet pump assembly comprises a first jet pump beam and a second jet pump beam, and positioning at least one ultrasonic phased array probe adjacent the bottom surface of the jet pump beam comprises:

positioning a first ultrasonic phased array probe adjacent the bottom surface of the first jet pump beam first arm;

positioning a second ultrasonic phased array probe adjacent the bottom surface of the first jet pump beam second arm;

positioning a third ultrasonic phased array probe adjacent the bottom surface of the second jet pump beam first arm; and positioning a fourth ultrasonic phased array probe adjacent the bottom surface of the second jet pump beam second arm.

17. A method in accordance with claim 16 wherein scanning the jet pump beam comprises:

scanning at least one of the transition portion and the radiused portion of the first jet pump beam first arm with the first ultrasonic phased array probe;

scanning at least one of the transition portion and the radiused portion of the first jet pump beam second arm with the second ultrasonic phased array probe;

scanning at least one of the transition portion and the radiused portion of the second jet pump beam first arm with the third ultrasonic phased array probe;

scanning at least one of the transition portion and the radiused portion of the second jet pump beam second arm with the fourth ultrasonic phased array probe.

18. A method in accordance with claim 10 wherein scanning at least one of the transition portion and the radiused portion of the jet pump beam comprises scanning at least one of the transition portion and the radiused portion of the jet pump beam with the at least one ultrasonic phased array probe so that a scanned volume of the jet pump beam comprises an area extending from the bolt opening to the end of the first beam arm and that extends from the top surface of the beam at least partially towards the bottom of the beam.

19. A method in accordance with claim 18 wherein scanning at least one of the transition portion and the radiused portion of the jet pump beam further comprises scanning at least one of the transition portion and the radiused portion of the jet pump beam with the at least one ultrasonic phased array probe so that a scanned volume of the jet pump beam further comprises an area extending from the bolt opening to the end of the second beam arm and extending from the top surface of the beam at least partially towards the bottom of the beam.

* * * * *